US 6,642,400 B2
Nov. 4, 2003

(12) United States Patent
Holtcamp et al.

(54) LINKED METALLOCENE COMPLEXES, CATALYST SYSTEMS, AND OLEFIN POLYMERIZATION PROCESSES USING SAME

(75) Inventors: Matthew W. Holtcamp, Huffman, TX (US); Laughlin G. McCullough, League City, TX (US)

(73) Assignee: Univation Technologies, LLC, Houston, TX (US)

( * ) Notice: Subject to any disclaimer, the term of this patent is extended or adjusted under 35 U.S.C. 154(b) by 133 days.

(21) Appl. No.: 09/963,840

(22) Filed: Sep. 26, 2001

(65) Prior Publication Data

US 2003/0069373 A1 Apr. 10, 2003

(51) Int. Cl.$^7$ .......................... C07F 17/00; B01J 31/00; C08F 4/44
(52) U.S. Cl. .............................. 556/11; 556/12; 556/53; 526/160; 526/943; 502/103; 502/117
(58) Field of Search .............................. 556/11, 12, 53; 502/103, 117; 526/160, 943

(56) References Cited

U.S. PATENT DOCUMENTS

| | | | | |
|---|---|---|---|---|
| 5,372,980 A | * | 12/1994 | Davis | 502/103 |
| 5,830,958 A | | 11/1998 | Peifer et al. | 526/113 |
| 6,153,776 A | | 11/2000 | Patton et al. | 556/11 |
| 6,239,299 B1 | | 5/2001 | Schottenberger et al. | 556/28 |
| 6,262,197 B1 | | 7/2001 | Aulbach et al. | 526/127 |

FOREIGN PATENT DOCUMENTS

EP 0 953 581 A1 3/1999

OTHER PUBLICATIONS

*Journal of Molecular Catalysis: A Chemical*, W. Spaleck et al., 128 (1998) 279–287.

* cited by examiner

*Primary Examiner*—Porfirio Nazario-Gonzalez
(74) *Attorney, Agent, or Firm*—Lisa Kimes Jones; Kevin M. Faulkner

(57) ABSTRACT

Disclosed are metallocene complexes containing two or more metallocene components where the components may be independently bridged or unbridged. In particular, the invention provides metallocene complexes including a bridged metallocene component linked to an unbridged metallocene component where a ligand structure of the unbridged metallocene component is linked to the bridging group of the bridged metallocene component. The invention provides metallocene complexes including a first unbridged metallocene component linked to second unbridged metallocene component via their ligand structures. The invention also provides metallocene complexes including a bridged metallocene component linked to a second bridged metallocene component via their ligand structures. The invention further provides methods of preparing the linked metallocene complexes described above, catalyst systems including these linked metallocene complexes, polymerization processes utilizing these complexes, and polymers made thereby.

32 Claims, No Drawings

LINKED METALLOCENE COMPLEXES, CATALYST SYSTEMS, AND OLEFIN POLYMERIZATION PROCESSES USING SAME

FIELD OF THE INVENTION

The present invention relates to polymerization catalyst complexes, catalyst systems including these catalyst complexes, and to their use in the polymerization of olefins. In particular, the present invention relates to metallocene complexes, which include two or more metallocene components linked together. Specifically, the metallocene components are linked together through the ligand structure of at least one of the metallocenes. The present invention also relates to catalyst systems containing these metallocene complexes and to their use in olefin polymerization processes.

BACKGROUND OF THE INVENTION

Use of metallocene based catalyst systems in polymerization processes to produce a diverse array of new polymers for a wide variety of applications and products is well known in the art. Polymers produced by metallocene catalysts have excellent properties such as mechanical strength and transparency. However, these polymers are typically more difficult to process.

To obtain polymer products having improved physical properties as well as easier processing polymers, the industry has focused on the physical blending of two or more polymers in the hopes that the polymer blend will exhibit the best characteristics of its component polymers. Others have looked at using two or more reactors to produce blends in situ in the reactor or at using two or more catalysts to produce the desired polymer product.

Utilizing two different catalysts, however, typically results in a polymer whose characteristics cannot be predicted from those of the polymers that each catalyst would produce if utilized separately. This unpredictability occurs, for example, from competition or other influence between the catalyst or catalyst systems used. In addition, these polymers typically do not have a preferred balance of processability and strength properties. Therefore, there is need in the art for metallocene catalyst systems capable of producing processable polymers having desirable combinations of processing, mechanical and optical properties.

U.S. Pat. No. 5,830,958 discloses a process for preparing polynuclear metallocenes by reacting a metallocene in which one of the cyclopentadienyl containing radicals has a substitutent having olefinic or acetylenic unsaturation, with a second metallocene having a metal which comes from groups VIb to Vib and a metal-hydride bond.

U.S. Pat. No. 6,153,776 discloses a Group 3–6 or Lanthanide metal complex possessing two metal centers, catalyst derived therefrom by combining the same with strong Lewis acids, Bronsted acid salts, salts containing a cationic oxidizing agent or subject to bulk electrolysis in the presence of compatible inert non-coordinating anions.

U.S. Pat. No. 6,262,197 discloses a metallocene compound containing at least two metallocene fragments L—$MX_2$—L.

EP 0 953 581 A1 discloses a supported metallocene having ligands linked to $R'OSiR''_3$ groups where $R'$ is a divalent aliphatic hydrocarbon group containing from 1–20 carbon atoms optionally containing heteroatoms or a $SiR''_2$ group, and $R''$ is a $C_{1-20}$ alkyl, a $C_{3-20}$ cycloalkyl, $C_{6-20}$ aryl, $C_{3-20}$ alkenyl $C_{7-20}$ arylalkyl, $C_{8-20}$ arylalkenyl, or a $C_{7-20}$ alkylaryl linear or branched group.

Spalek et al., in *New Bridged Zirconocenes for Olefin Polymerization: Binuclear and Hybrid Structures,* Journal of Molecular Catalysis A: Chemical 128 (1998) 279–287, disclose bridged bisindenyl zirconocenes for the polymerization of liquid propylene.

SUMMARY OF THE INVENTION

In one aspect, the invention provides a linked metallocene complex having at least one bridged metallocene component linked to at least one unbridged metallocene component where the ligand structure of an unbridged metallocene component is connected to the bridging group of a bridged metallocene component.

In another aspect, the invention provides a linked metallocene complex having a first bridged metallocene component linked to an unbridged metallocene component linked to a second bridged metallocene component where a first ligand structure of the unbridged metallocene component is connected to the bridging group of the first bridged metallocene component, and a second ligand structure of the unbridged metallocene component is connected to the bridging group of the second bridged metallocene component.

In another aspect, the invention provides a linked metallocene complex having a first unbridged metallocene component linked to second unbridged metallocene component where a ligand structure of the first unbridged metallocene component is linked to a ligand structure of the second unbridged metallocene component.

In another aspect, the invention provides a linked metallocene complex having a first unbridged metallocene component linked to second unbridged metallocene component linked to a third unbridged metallocene component where a ligand structure of the first unbridged metallocene component is linked to a first ligand structure of the second unbridged metallocene component and where a second ligand structure of the second unbridged metallocene component is linked to a ligand structure of the third unbridged metallocene component.

In another aspect, the invention provides a linked metallocene complex containing a first bridged metallocene component linked to a unbridged metallocene component linked to a second bridged metallocene component where a ligand structure of the first bridged metallocene is linked to a first ligand structure of the unbridged metallocene and where a ligand structure of the second bridged metallocene is linked to a second ligand structure of the unbridged metallocene component.

The invention also provides methods of preparing the linked metallocene complexes described above, catalyst systems including these linked metallocene complexes, polymerization processes utilizing these complexes, and polymers made thereby.

DETAILED DESCRIPTION

New catalyst systems including structurally linked metallocenes, and synthetic routes to prepare such linked metallocenes have been discovered. Preferably, the linked metallocene includes two or more metallocene structures connected through the ligand framework of at least one of the metallocene structures.

For the purposes of this patent specification, the term "catalyst" refers to a metal compound, that when combined with an activator, polymerizes olefins. The term "activator" is used interchangeably with the term "co-catalyst", and the term "catalyst system" refers to the combination of catalyst, activator, and optionally a support material.

Linked Metallocene Complexes of the Invention

In one embodiment, the linked metallocene complex contains at least one bridged metallocene component linked to at least one unbridged metallocene component where the ligand structure of the unbridged metallocene component is connected to the bridging group of the bridged metallocene component. In this embodiment, the two ligand structures are linked together via a linking group.

In another embodiment, the linked metallocene complex is represented by Formula I.

Formula I

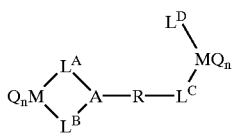

In Formula I, each M is independently a metal atom from the Periodic Table of the Elements and may be a Group 3 to 12 metal or a metal from the lanthanide or actinide series, preferably each M is independently a Group 3 to 10 transition metal, more preferably each M is independently a Group 4, 5 or 6 transition metal, and even more preferably each M is independently zirconium, hafnium or titanium. Most preferably, each M is zirconium.

In Formula I, each Q represents a leaving group bonded to each M. For the purposes of this patent specification and appended claims the term "leaving group" is any ligand that can be abstracted from a metallocene catalyst compound to form a metallocene catalyst cation capable of polymerizing one or more olefin(s). Each Q is independently a monoanionic ligand, or two radicals Q together form a divalent anionic chelating ligand. In one embodiment, Q is a monoanionic labile ligand having a sigma-bond to M. In a preferred embodiment, two monoanionic leaving groups Q are bonded to each M.

In one embodiment, each Q is independently a halogen, a hydrocarbyl radical, a hydrocarbyl radical having from 1 to 20 carbon atoms, a hydride, a carboxylate, a diene, an ether, an amide, or a phosphide. Preferably, each Q is independently selected from halogen, $C_1$–$C_6$ alkyl groups, $C_6$–$C_{10}$ aryl groups, $C_7$–$C_{12}$ arylalkyl groups and $C_7$–$C_{12}$ alkylaryl groups.

In Formula I, each n is independently 0, 1, or 2, depending on the oxidation state of the metal, such that Formula (I) above represents a neutral compound. In a preferred embodiment, each n is 2.

In Formula I, $L^A$, $L^B$ are bonded to a first metal atom M, and $L^C$ and $L^D$ are bonded to a second metal atom M. $L^A$, $L^B$, $L^C$ and $L^D$ are aromatic ring systems, which may be the same or different, and are typically composed of atoms selected from Groups 13 to 16 of the Periodic Table of Elements. Preferably the atoms are selected from carbon, nitrogen, oxygen, silicon, sulfur, phosphorus, germanium, boron, aluminum and combinations thereof. Most preferably, the aromatic rings or ring systems are unsubstituted or substituted, cyclopentadienyl and cyclopentadienyl-type ligands where "cyclopentadienyl-type" means a ligand comprising a cyclopentadienyl, or a related structure, for example, a structure wherein one or more carbon atoms of a cyclopentadienyl ligand are replaced by one or more hetereoatoms such as, e.g., N, O and S. Non-limiting examples thereof include unsubstituted and substituted cyclopentadienyl, indenyl, benzindenyl, fluorenyl, azulenyl, pyrrolyl, pyrazolyl, carbazolyl and borabenzene ligands and the like, including hydrogenated versions thereof, for example, tetrahydroindenyl, tetrahydrofluorenyl and octahydrofluorenyl ligands.

In one embodiment, $L^A$, $L^B$, $L^C$ and $L^D$ are each independently selected form cyclopentadienyl, indenyl, fluorenyl and benzindenyl ligands as well as partially hydrogenated forms thereof, for example, tetrahydroindenyl. Also, these ring systems may be unsubstituted or substituted as described below.

In another embodiment, $L^A$, $L^B$, $L^C$ and $L^D$ are optionally and/or independently substituted with one or more substituent groups. Non-limiting examples of substituent groups are linear, branched and cyclic alkyl, alkenyl and alkynyl radicals, aryl, arylalkyl and alkylaryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- and dialkylcarbamoyl radicals, acyloxy radicals, acylamino radicals, aroylamino radicals and combinations thereof. In one embodiment the substituent groups, if any, have up to 50 non-hydrogen atoms, for example, from 1 to 30 carbon atoms, more preferably from 1 to 20 carbon atoms, and even more preferably from 1 to 12 carbon atoms. Moreover these substituent groups may also be halogenated, e.g., fluorinated and/or chlorinated.

Illustrative, non-limiting examples of optional substituents for $L^A$, $L^B$, $L^C$ and $L^D$ include methyl, ethyl, propyl, butyl, pentyl, hexyl, cyclopentyl, cyclohexyl, benzyl, phenyl, tolyl and xylyl groups and the like, including all their isomers, for example tertiary butyl, isopropyl, and the like. Further non-limiting examples of other possible substituents include hydrocarbyl substituted organometalloid radicals such as, e.g., trimethylsilyl, trimethylgermyl, methyldiethylsilyl and the like; halocarbyl-substituted organometalloid radicals including tris(trifluoromethyl)silyl, methyl-bis(difluoromethyl)silyl, bromomethyl-dimethylgermyl and the like; and disubstituted boryl radicals including dimethylboryl and the like; disubstituted pnictogen radicals including dimethylamino, dimethylphosphino, diphenylamino, methylphenylphosphino and the like; and chalcogen radicals including methoxy, ethoxy, propoxy, phenoxy, methylthio, ethylthio and the like. In general, the non-hydrogen atoms of the substituents are selected from carbon, silicon, boron, aluminum, nitrogen, phosphorus, oxygen, tin, sulfur, germanium and the halogens. Also, at least two substituent groups, preferably two adjacent substituent groups, may be joined to form a ring structure having from 3 to 30 members selected from carbon, nitrogen, oxygen, phosphorous, silicon, germanium, aluminum, boron and combinations thereof.

In another embodiment, $L^A$, $L^B$, $L^C$ and $L^D$ are each independently selected form substituted or unsubstituted cyclopentadienyl, indenyl, fluorenyl and benzindenyl ligands as well as partially hydrogenated forms thereof, for example, tetrahydroindenyl. In another embodiment the optional substituents are selected from alkyl groups having 1 to 4 carbon atoms.

In Formula I, A is a bridging group connecting $L^A$ and $L^B$. A is also connected to $L^C$ via R. In one embodiment, bridging group A contains at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A contains a carbon, silicon or germanium atom, most preferably A contains at least one silicon atom or at least one carbon atom. In another embodiment, A may also be a long bridging group containing 2 or more Group 13 to Group 16 atoms, preferably 3 or more Group 13 to Group 16 atoms. The bridging group A may also contain substituent groups, as defined above, including halogens. In another embodiment, bridging group A is represented by R'C, R'Si, R'SiR'Si, R'Ge, P, or R'$_2$Si—O—R'$_2$Si, where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system.

In Formula I, R is a linking group connecting A to $L^C$. In one embodiment, linking group R is a substituted or unsubstituted hydrocarbyl group, as defined below, having from 1 to 100,000 carbon atoms, 1 to 10,000 carbon atoms, 1 to 1000 carbon atoms, 1 to 500 carbon atoms, 1 to 100 carbon atoms, 1 to 20 carbon atoms, 1 to 10 carbon atoms, or 1 to 6 carbon atoms. In another embodiment, linking group R is a substituted or unsubstituted hydrocarbyl group containing more than 3 carbon atom, preferably more than 6, more than 20, or more than 100 carbon atoms. In another embodiment, linking group R is a substituted or unsubstituted alkyl, alkenyl, alkoxy or aryl group, as defined below. In another embodiment, R is a substituted or unsubstituted alkyl group having from 1 to 100,000 carbon atoms, 1 to 1000 carbon atoms, 1 to 500 carbon atoms, 1 to 100 carbon atoms, 1 to 20 carbon atoms, 1 to 10 carbon atoms, or 1 to 6 carbon atoms. In another embodiment linking group R contains at least one heteroatom selected from Groups 13 to 16, and may also include a heterocyclic group. Preferably, the at least one heteroatom is selected from N, P, O, and S or any subset thereof.

In another embodiment, the linked metallocene complex of Formula I includes a first bridged metallocene component which is a good comonomer incorporating metallocene structure and a second unbridged metallocene component which is a poor comonomer incorporator. For purposes of this specification and claims a poor comonomer incorporator is defined as a metallocene catalyst component which incorporates less than 6 mole % comonomer, preferably less than 4 mole % comonomer, preferably less than 2 mole % comonomer, and a good comonomer incorporator is a metallocene catalyst component which incorporates more comonomer relative to the poor comonomer incorporator.

In another embodiment, a linked metallocene complex of Formula I may be prepared, for example, by forming a cyclopentadiene or cyclopentadiene-type ligand having a halogenated alkyl moiety. This is accomplished by reacting the substituted or unsubstituted cyclopentadiene or a cyclopentadiene-type compound with an alkali metal (Li, Na, K) salt such as methyllithium or n-butyllithium in a suitable solvent, such as tetrahydrofuran, to form the corresponding lithium cyclopentadienide. The lithium cyclopentadienide is then reacted with a compound of the formula X—R—A—X$_2$R where X is a halogen, preferably X is chloride; each R is independently as defined above; A is as defined above, preferably A is a silicon or a germanium atom, and more preferably A is a silicon atom.

The product of the above, which may be represented by X—R—AX-Cp1 where Cp1 represents a first cyclopentadiene or cyclopentadiene-type structure, is reacted with a second lithium cyclopentadienide or cyclopentadienide-type structure, Cp2, which may be the same or different from Cp1, yielding X—R—ACp2Cp1.

The product, X—R—ACp2Cp1, obtained above is then reacted with a metal amide to yield a metallocene amide containing a reactive halogenated alkyl moiety. For example X—R—ACp2Cp1 is combined with a metal amide having the formula M(NR$_2$)$_4$, where for purposes of this embodiment, M is metal atom, preferably a Group 4 metal, preferably Zr or Hf and more preferably Zr, and R is a alkyl group having form 1 to 6 carbon atoms. The amide ligands, used here, serve as a protecting group to retain the structural identity of the metallocene group during the building, or attaching, of subsequent metallocene components. For example the —NR2 ligands protect the metal site from undesirable reactions such as butylation or reduction. These protective groups may be replaced later as described below.

The product obtained above is then reacted with a third lithium cyclopentadienide or a cyclopentadienide-type structure (Cp3), which may be the same or different as Cp1 and/or Cp2, yielding H-Cp3-R—A(Cp1)(Cp2)M(NR$_2$)$_2$, which may then be deprotonated for example, via butyl lithium, producing Li-Cp3-R—A(Cp1)(Cp2)M(NR$_2$)$_2$.

Reaction of Li-Cp3-R—A(Cp1)(Cp2)M(NR$_2$)$_2$ with Cp4MCl$_3$ yields Cp4MCl$_2$Cp3-R—A(Cp1)(Cp2)M(NR$_2$)$_2$, where Cp4 is a fourth substituted or unsubstituted cyclopentadienide or cyclopentadienide-type structure which may be the same or different for Cp1 and/or Cp2 and/or Cp3.

Cp4MCl$_2$Cp3-R—A(Cp1)(Cp2)M(NR$_2$)$_2$ may then, for example, be reacted with excess chlorotrimethylsilane to yielding Cp4MCl$_2$Cp3-R—A(Cp1)(Cp2)MCl$_2$.

In one embodiment, the linked metallocene complex contains a first bridged metallocene component linked to an unbridged metallocene component linked to a second unbridged metallocene component. In this embodiment, a first ligand structure of the unbridged metallocene component is connected to the bridging group of the first bridged metallocene component, and a second ligand structure of the unbridged metallocene component is connected to the bridging group of the second bridged metallocene component.

In another embodiment, the linked metallocene complex is represented by Formula II.

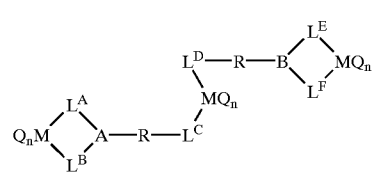

Formula II

In Formula II, metal atoms M, leaving groups Q, n, ligands $L^A, L^B, L^C, L^D$, bridging group A and linking groups R are defined as above in Formula I. $L^E$ and $L^F$ are independently defined the same as $L^A, L^B, L^C$ and $L^D$ were defined in Formula I. B is a bridging group and is defined the same as A in Formula I. B may be the same or different from A.

In one embodiment, in Formula II, $L^A, L^B, L^C, L^D L^E$ and $L^F$ are each a substituted or unsubstituted cyclopentadienyl, indenyl, fluorenyl and benzindenyl ligands as well as partially hydrogenated forms thereof, for example, tetrahydroindenyl. In addition, in another embodiment, $L^A$ is the same as $L^E$, $L^B$ is the same as $L^F$, $L^C$ is the same as $L^D$, and the metal connected to $L^A$ and $L^B$ is the same as the metal atom connected to $L^E$ and $L^F$. In another embodiment, the optional substituents are selected from alkyl groups having 1 to 4 carbon atoms.

In another embodiment, the linked metallocene complex of Formula II includes a first and second bridged metallocene component which are good comonomer incorporating metallocenes and a unbridged metallocene component which is a poor comonomer incorporator relative to the good comonomer incorporator.

In another embodiment, the linked metallocene complex of Formula II may be prepared, for example, by forming a cyclopentadiene or cyclopentadiene-type ligand having a halogenated alkyl moiety. This is accomplished by reacting the substituted or unsubstituted cyclopentadiene or a cyclopentadiene-type compound with an alkali metal (Li, Na, K) salt such as methyllithium or n-butyllithium in a suitable solvent, such as tetrahydrofuran, to form the corresponding lithium cyclopentadienide. The lithium cyclopentadienide is then reacted with a compound of the formula X—R—A—X$_2$R where X is a halogen, preferably X is chloride; each R is independently as defined above; A is as defined above, preferably A is a silicon or a germanium atom, and more preferably A is a silicon atom.

The product of the above, which may be represented by X—R—AX-Cp1 where Cp1 represents a first cyclopentadiene or cyclopentadiene type structure, is reacted with a second lithium cyclopentadienide or cyclopentadienide type structure, Cp2, which may be the same or different form Cp1, yielding X—R—ACp2Cp1.

The product, X—R—ACp2Cp1, obtained above is then reacted with a metal amide, preferably a Group 4 metal amide to yield a metallocene amide containing a reactive halogenated alkyl moiety. For example, X—R—ACp2Cp1 is combined with a metal amide having the formula M(NR$_2$)$_4$, where for purposes of this embodiment, M is a Group 4 metal, preferably Zr or Hf and more preferably Zr, and R is a alkyl group having form 1 to 6 carbon atoms.

The product of the above reaction is reacted with a third lithium cyclopentadienide or a cyclopentadienide-type structure (Cp3), which may be the same or different as Cp1 and/or Cp2, yielding H-Cp3-R—A(Cp1)(Cp2)M(NR$_2$)$_2$, which may then be deprotonated, for example, via butyl lithium producing Li-Cp3-R—A(Cp1)(Cp2)Zr(NR$_2$)$_2$.

Two equivalents of the product, Li-Cp3-R—A(Cp1)(Cp2)Zr(NR$_2$)$_2$, is then reacted with MCl$_4$ yielding Cl$_2$M[Cp3-R—A(Cp1)(Cp2)Zr(NMe$_2$)$_2$]$_2$.

Cl$_2$M[Cp3-R—A(Cp1)(Cp2)Zr(NMe$_2$)$_2$]$_2$ is then reacted with excess chlorotrimethylsilane yielding Cl$_2$Zr[Cp3-R—A(Cp1)(Cp2)ZrCl$_2$]$_2$.

In one embodiment, the linked metallocene complex contains a first unbridged metallocene component linked to second unbridged metallocene component where a ligand structure of the first unbridged metallocene component is linked to a ligand structure of the second unbridged metallocene component.

In another embodiment, the linked metallocene complex is represented by Formula III.

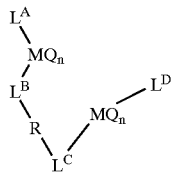

Formula III

In Formula III, metal atoms M, leaving groups Q, n, ligands $L^A$, $L^B$, $L^C$, $L^D$ and linking group R are defined as above in Formula I.

In another embodiment, the linked metallocene complex of Formula III includes a metallocene component which is a good comonomer incorporating metallocene structure, as defined above, and a metallocene component which is a poorer comonomer incorporator than the first. For example, Hf analogs are known to be better comonomer incorporators then their Zr counterparts.

In another embodiment, the linked metallocene complex of Formula III may be prepared, for example, by forming a cyclopentadiene or cyclopentadiene-type ligand having a halogenated alkyl moiety. This is accomplished by reacting the substituted or unsubstituted cyclopentadiene or a cyclopentadiene-type compound with an alkali metal (Li, Na, K) salt such as methyllithium or n-butyllithium in a suitable solvent, such as tetrahydrofuran, to form the corresponding lithium cyclopentadienide. The lithium cyclopentadienide is then reacted with a compound of the formula Cl—R—Br where each R is independently as defined above; A is as defined above, preferably A is a silicon or a germanium atom, and more preferably A is a silicon atom.

The product, X—R-Cp1, where Cp1 represents a first cyclopentadiene or cyclopentadiene-type structure, X is a halogen, and R is as defined above, is then reacted with a metal amide, preferably a Group 4 metal amide, to yield a metallocene amide containing a reactive halogenated alkyl moiety. Cl—R-Cp1 is combined with a metal amide having the formula M(NR$_2$)$_4$, where for purposes of this embodiment, M is a Group 4 metal, preferably Zr or Hf and more preferably Zr, and R is a alkyl group having form 1 to 6 carbon atoms.

The product of the above reaction, (Cl—R-Cp1)M(NR$_2$)$_3$, is then reacted with chlorotrimethylsilane yielding (Cl—R-Cp1)M(NR$_2$)$_2$Cl.

The above product is reacted with two equivalents of a lithium cyclopentadienide or cyclopentadienide-type structure yielding (HCp2-R -Cp1)Cp2M(NR$_2$)$_2$. Where Cp2 represents a second cyclopentadiene or cyclopentadiene-type structure which may be the same or different from Cp1.

The product, (HCp2-R-Cp1)Cp2M(NR$_2$)$_2$, may then be reacted, for example, with butyl lithium producing (LiCp2-R-Cp1)Cp2M(NR$_2$)$_2$ which may be further reacted with Cp3MCl$_3$, where Cp3 represents a third cyclopentadiene or cyclopentadiene-type structure, which may be the same or different from Cp1 and/or Cp2, yielding (Cl$_2$MCp3Cp2-R-Cp1)Cp2M(NR$_2$)$_2$.

The above reaction product may then be reacted with chlorotrimethylsilane producing the product (Cl$_2$MCp3Cp2-R-Cp1)Cp2MCl$_2$.

In one embodiment, the linked metallocene complex contains a first unbridged metallocene component linked to second unbridged metallocene component linked to a third unbridged metallocene component where a ligand structure of the first unbridged metallocene component is linked to a ligand structure of the second unbridged metallocene component and where a ligand structure of the second unbridged metallocene component is linked to a ligand structure of the third unbridged metallocene component. In another embodiment, the linked metallocene complex is represented by Formula IV.

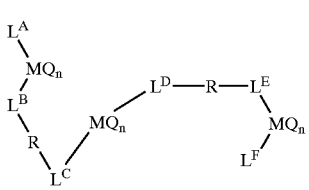

Formula IV

In Formula IV, metal atoms M, leaving groups Q, n, ligands $L^A$, $L^B$, $L^C$, $L^D$, $L^E$, $L^F$ and linking groups R are defined the same as in Formulae I and II.

In another embodiment, the linked metallocene complex of Formula IV includes metallocene component(s) which are good comonomer incorporators as well as those which are poor comonomer incorporators.

In one embodiment, in Formula IV, $L^A$, $L^B$, $L^C$, $L^D$ $L^E$ and $L^F$ are each a substituted or unsubstituted cyclopentadienyl, indenyl, fluorenyl and benzindenyl ligands as well as partially hydrogenated forms thereof, for example, tetrahydroindenyl. In addition, in another embodiment, $L^A$ is the same as $L^F$, $L^B$ is the same as $L^E$, $L^C$ is the same as $L^D$, and the metal atom connected to $L^A$ and $L^B$ is the same as the metal atom connected to $L^E$ and $L^F$. In another embodiment, the optional substituents are selected from alkyl groups having 1 to 4 carbon atoms.

In another embodiment, the linked metallocene complex of Formula IV may be prepared, for example, by forming a cyclopentadiene or cyclopentadiene-type ligand having a halogenated alkyl moiety. This is accomplished by reacting the substituted or unsubstituted cyclopentadiene or a cyclopentadiene-type compound with an alkali metal (Li, Na, K) salt such as methyllithium or n-butyllithium in a suitable solvent, such as tetrahydrofuran, to form the corresponding lithium cyclopentadienide. The lithium cyclopentadienide is then reacted with a compound of the formula Cl—R—Br where R is as defined above. Preferably, R is an alkyl group as defined above in Formula I.

The product, Cl—R-Cp1 is then reacted with a Group 4 metal amide to yield a metallocene amide containing a reactive halogenated alkyl moiety. Cl—R -Cp1 is combined with a metal amide having the formula $M(NR_2)_4$, where for purposes of this embodiment, M is a Group 4 metal, preferably Zr or Hf and more preferably Zr, and R is a alkyl group having form 1 to 6 carbon atoms to form $(X—R-Cp1)_2 M(NR_2)_2$.

The $(X—R-Cp1)_2 M(NR_2)_2$ product of the above reaction is reacted with a lithium cyclopentadienide or a cyclopentadienide-type structure yielding $(H-Cp2-R-Cp1)_2 M(NR_2)_2$, where Cp2 is a second cyclopentadiene or cyclopentadiene-type structure, which may be the same or different from Cp1. The product of this reaction may then be deprotonated, for example via butyl lithium, producing $(Li-Cp2-R-Cp1)2M(NR_2)_2$.

The product, $(Li-Cp2-R-Cp1)_2M(NR_2)_2$, is reacted with $Cp3MCl_3$ yielding $(Cp3MCl_2Cp2-R-Cp1)_2M(NMe_2)_2$, where Cp3 is a third cyclopentadiene or cyclopentadiene-type structure, which may be the same or different from Cp1 and/or Cp2.

$(Cp3MCl_2Cp2-R-Cp1)_2M(NR_2)_2$ may then be reacted, for example, with excess chlorotrimethylsilane yielding $(Cp3MCl_2Cp2-R-Cp1)_2MCl_2$.

In one embodiment, the linked metallocene complex contains a first bridged metallocene component linked to a unbridged metallocene component linked to a second bridged metallocene component where a ligand structure of the first bridged metallocene is linked to a first ligand structure of the unbridged metallocene and where a ligand structure of the second bridged metallocene is linked to a second ligand structure of the unbridged metallocene component. In this embodiment, the linked metallocene complex is represented by Formula V.

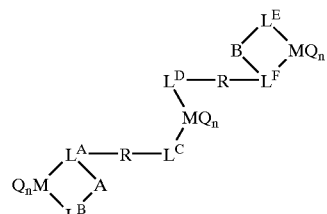

Formula V

In Formula V, metal atoms M, leaving groups Q, n, ligands $L^A$, $L^B$, $L^C$, $L^D$, $L^E$, $L^F$, bridging groups A and B, and linking groups R are defined the same as in Formulae I and II.

In one embodiment, in Formula II, $L^A$, $L^B$, $L^C$, $L^D$ $L^E$ and $L^F$ are each a substituted or unsubstituted cyclopentadienyl, indenyl, fluorenyl and benzindenyl ligands as well as partially hydrogenated forms thereof, for example, tetrahydroindenyl. In addition, in another embodiment, $L^A$ is the same as $L^F$, $L^B$ is the same as $L^E$, $L^C$ is the same as $L^D$, and the metal atom connected to $L^A$ and $L^B$ is the same as the metal atom connected to $L^E$ and $L^F$. In another embodiment, the optional substituents are selected from alkyl groups having 1 to 4 carbon atoms.

In another embodiment, the linked metallocene complex of Formula II includes a first and second bridged metallocene component which is a good comonomer incorporating metallocene structure and an unbridged metallocene component which is a poor comonomer incorporator.

In another embodiment, the linked metallocene complex of Formula V may be prepared, for example, by forming a cyclopentadiene or cyclopentadiene-type ligand having a halogenated alkyl moiety. This is accomplished by reacting the substituted or unsubstituted cyclopentadiene or a cyclopentadiene-type compound with an alkali metal (Li, Na, K) salt such as methyllithium or n-butyllithium in a suitable solvent, such as tetrahydrofuran, to form the corresponding lithium cyclopentadienide. The lithium cyclopentadienide is then reacted with a compound of the formula Cl—R—Br where each R is independently as defined above; A is as defined above, preferably A is a silicon or a germanium atom, and more preferably A is a silicon atom.

The product, X—R-Cp1, obtained above is then reacted with a metal amide, preferably a Group 4 metal amide, to yield a metallocene amide containing a reactive halogenated alkyl moiety. Cp1 is a cyclopentadiene or cyclopentadiene-type structure. X—R-Cp1 is combined with a metal amide having the formula $M(NR_2)_4$, where for purposes of this embodiment, M is a Group 4 metal, preferably Zr or Hf and more preferably Zr, and R is a alkyl group having form 1 to 6 carbon atoms.

The product of the above reaction is reacted with a lithium cyclopentadienide or a cyclopentadienide-like structure yielding $(H-Cp2-R-Cp1)_2M(NR_2)_2$, which may then be deprotonated via butyl lithium producing $(Li-Cp2-R-Cp1)_2 M(NR_2)_2$. Cp2 is a cyclopentadiene or cyclopentadiene-type structure, which may be the same or different from Cp1.

The product, $(Li-Cp2-R-Cp1)_2M(NR_2)_2$, is reacted with $X_2A$ yielding $(X—A-HCp2-R-Cp1)_2M(NR_2)_2$ which may be further reacted with a lithium cyclopentadienide or a cyclopentadienide-like structure yielding $(HCp3-A-HCp2-R-Cp1)_2M(NR_2)_2$, where Cp3 is a cyclopentadiene or cyclopentadiene-type structure, which may be the same or different from Cp1 and/or Cp2.

$(HCp3-A-HCp2-R-Cp1)_2M(NR_2)_2$ may be reacted with $M(NR_2)_4$ yielding $((R_2N)_2MCp3-A-Cp2-R-Cp1)_2M(NR_2)_2$ which may be further treated with chlorotrimethylsilane yielding $(Cl_2MCp3-A-Cp2-R-Cp1)_2MCl_2$.

Referring to Formulae I to V above, in preferred embodiments, M is a metal selected from Groups 3 to 10 and the lanthanide series of the Periodic Table of Elements, preferably a Group 3 to 6, more preferably a Group 4 metal such as Zr and Hf; The ligands $L^A$, $L^B$, $L^C$, $L^D$, $L^E$ and $L^F$, if present, are independently selected from substituted or unsubstituted cyclopentadienyl ligands and cyclopentadienyl-type ligands, preferably unsubstituted or substituted cyclopentadienyl, indenyl or fluorenyl ligands; A and/or B comprise carbon, silicon, or germanium; R is a substituted or unsubstituted alkyl, alkenyl, alkoxy or aryl group each is Q independently selected from halogen and alkyl groups, or two radicals Q together form a divalent anionic chelating ligand; and n is 0, 1 or 2, depending on the formal oxidation state of M.

The term "alkyl", as utilized herein, means a straight-chain, branched-chain or cyclic alkyl radical. Examples of such radicals include, but are not limited to, methyl, ethyl, n-propyl, isopropyl, n-butyl, isobutyl, sec-butyl, tert-butyl, pentyl, iso-amyl, hexyl, 2-ethylhexyl, octyl, cyclopentyl, cyclohexyl and the like. The cyclic alkyl radicals may be substituted with one or more straight-chain and/or branched-chain alkyl radicals (i.e., may be alkylcycloalkyl radicals such as, e.g., methylcyclohexyl etc.). Conversely, the straight-chain and branched-chain alkyl radicals may be substituted with one or more cyclic alkyl radicals (i.e., may be cycloalkylalkyl radicals such as cyclohexylmethyl etc.). Moreover, unless indicated otherwise, the above alkyl radicals may be substituted by one or more groups preferably and independently selected from halogen (e.g., F, Cl, Br), alkoxy (e.g., methoxy, ethoxy, propoxy, butoxy and the like), hydroxy, amino, monoalkylamino (e.g., methylamino, ethylamino, propylamino and the like) and dialkylamino (e.g., dimethylamino, diethylamino, dipropylamino, diisopropylamino, piperidino and the like) and trihydrocarbylsilyl (e.g., trimethylsilyl, triphenylsilyl and the like). Unless otherwise stated, the above definition of the term "alkyl" also applies to groups comprising one or more alkyl radicals.

The term "alkenyl", as utilized herein, means "alkyl" as defined above having one or more double and/or triple bonds. Examples of alkenyl radicals include, but are not limited to, ethenyl, propenyl, allyl, butenyl, propargyl, 1,4-butadienyl, isopropenyl, cyclopentenyl, cyclohexenyl, cyclooctenyl, cyclopentadienyl, cyclohexadienyl, cyclooctadienyl and the like.

The term "alkoxy", as utilized herein, means an alkyl or alkenyl ether radical wherein the terms "alkyl" and "alkenyl" are as defined above. Examples of suitable alkyl ether radicals include, but are not limited to, methoxy, ethoxy, n-propoxy, isopropoxy, n-butoxy, iso-butoxy, sec-butoxy, tert-butoxy, allyloxy, trifluoromethoxy and the like.

The term "aryl", as utilized herein, means an aromatic radical, for example, a phenyl, naphthyl, azulenyl, phenanthryl or anthracenyl radical and the like which optionally contains one or more (e.g., 2 or 3) heteroatoms (preferably selected from N, O and S and combinations thereof) in the ring and/or carries one or more identical or different substituents, for example, alkoxy, aryl, halogen, hydroxy, amino, monoalkylamino, dialkylamino, nitro, trihydrocarbylsilyl, alkyl-CO, alkylsulfonyl, alkyl-OCO etc., these terms being as defined herein. Illustrative, non-limiting examples of aryl radicals are phenyl, naphthyl, fluorenyl, chlorophenyl, dichlorophenyl, fluorophenyl, perfluorophenyl, hydroxyphenyl, anisyl, biphenyl, nitrophenyl, acetylphenyl, aminophenyl, pyridyl, pyridazyl, quinolyl, and the like. When carbon numbers are given herein for aryl radicals, ring heteroatoms are counted as carbon atoms. Unless otherwise stated, the above definition of the term "aryl" also applies to groups which comprise one or more aryl radicals. For example, the term "aryloxy" means an aryl ether radical wherein the term "aryl" is as defined above.

The term "hydrocarbyl", as utilized herein, encompasses alkyl, alkenyl, arylalkyl arylalkenyl and alkylaryl groups wherein the terms "alkyl", "alkenyl" and "aryl" are as defined above. Preferred hydrocarbyl groups comprise 1 to 100,000 carbon atoms, 1 to 10,000 carbon atoms, 1 to 1000 carbon atoms, 1 to 500 carbon atoms, 1 to 100 carbon atoms, 1 to 20 carbon atoms, 1 to 10 carbon atoms, or 1 to 6 carbon atoms.

The term "halogen", as utilized herein, means fluorine, chlorine, bromine and iodine or any subset thereof.

Activators

The linked metallocene complexes of the invention are typically activated in various ways to yield compounds having a vacant coordination site that will coordinate, insert, and polymerize olefin(s). For the purposes of this patent specification and appended claims, the term "activator" is defined to be any compound which can activate any one of the catalyst complexes described above by converting the neutral catalyst complex to a catalytically active catalyst complex. Non-limiting examples of activators include aluminoxanes, aluminum alkyls, and ionizing activators, which may be neutral or ionic.

Aluminoxane and Aluminum Alkyl Activators

In one embodiment, an aluminoxane is utilized to activate the linked metallocene complexes of the invention. Aluminoxanes are generally oligomeric, cyclic or acyclic, compounds containing —Al(R)—O— subunits (generally about 6 to about 40), where R is an alkyl group. Illustrative, non-limiting examples of aluminoxanes include methylaluminoxane (MAO), modified methyl aluminoxane (MMAO), ethyl aluminoxane and isobutyl aluminoxane. Aluminoxanes may be produced by the hydrolysis of the respective trialkylaluminum compound. MMAO may be produced by the hydrolysis of trimethylaluminum and a higher trialkylaluminum compound such as triisobutylaluminum, and are generally more soluble in aliphatic solvents and more stable during storage. There are a variety of methods for preparing aluminoxane and modified aluminoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. Another aluminoxane is a MMAO cocatalyst type 3A (commercially available from Akzo Chemicals, Inc. under the trade name Modified Methylaluminoxane type 3A, covered under U.S. Pat. No. 5,041,584, fully incorporated herein by reference).

Illustrative, non-limiting examples of aluminum alkyl compounds which may be utilized as activators for the linked metallocene complexes of the invention include trimethylaluminum, triethylaluminum, triisobutylaluminum, tri-n-hexylaluminum, tri-n-octylaluminum and the like.

B. Ionizing Activators

It is also within the scope of this invention to use an ionizing or stoichiometric activator, neutral or ionic, such as, e.g., tri(n-butyl-ammoniumtetrakis(pentafluorophenyl) boron, a trisperfluorophenyl boron metalloid precursor or a trisperfluoronaphthyl boron metalloid precursor, polyhalogenated heteroborane anions (see, e.g., WO 98/43983, fully incorporated herein by reference), boric acid (see, e.g., U.S. Pat. No. 5,942,459, fully incorporated herein by reference) and combinations thereof. It is also within the scope of this invention to use neutral or ionic activators alone or in combination with aluminoxane or modified aluminoxane activators.

Non-limiting examples of neutral stoichiometric activators include tri-substituted boron, tellurium, aluminum, gallium, indium, and mixtures thereof. The three substituent groups may each independently be selected from alkyl, alkenyl, halogen, substituted alkyl, aryl, arylhalide, alkoxy and halide radicals. Preferably, the three groups are independently selected from halogen, mono- or polycyclic (including halosubstituted) aryl, alkyl, alkoxy and alkenyl radicals and combinations thereof. Preferred are alkyl groups having 1 to 20 carbon atoms, alkenyl groups having 1 to 20 carbon atoms, alkoxy groups having 1 to 20 carbon atoms and aryl groups having 6 to 20 carbon atoms (including substituted aryl groups). More preferably, the three groups are independently selected from alkyl groups having 1 to 4 carbon groups, phenyl and naphthyl groups. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are fully incorporated herein by reference.

In a preferred embodiment, the stoichiometric activators include a cation and an anion component, and may be represented Formula VI:

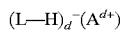
$(L-H)_d^+ (A^{d-})$   Formula VI wherein L is a neutral Lewis base; H is hydrogen; $(L-H)^+$ is a Bronsted acid $A^{d-}$ is a non-coordinating anion having the charge d–, and d is an integer from 1 to 3.

The cation component, $(L-H)_d^+$ may include Bronsted acids such as protons or protonated Lewis bases or reducible Lewis acids capable of protonating or abstracting a moiety, such as an alkyl or aryl group, from the catalyst precursor compound, resulting in a cationic transition metal species.

The activating cation $(L-H)_d^+$ may be a Bronsted acid, capable of donating a proton to the catalyst precursor resulting in a transition metal cation, including ammonium, oxonium, phosphonium, silylium species, and mixtures thereof, preferably ammonium species derived from methylamine, aniline, dimethylamine, diethylamine, N-methylaniline, diphenylamine, trimethylamine, triethylamine, N,N-dimethylaniline, methyldiphenylamine, pyridine, p-bromo-N,N-dimethylaniline and p-nitro-N,N-dimethylaniline; phosphonium species derived from triethylphosphine, triphenylphosphine, and diphenylphosphine; oxonium species derived from ethers such as dimethyl ether, diethyl ether, tetrahydrofuran and dioxane; sulfonium species derived from thioethers, such as diethyl thioether and tetrahydrothiophene; and mixtures thereof. The activating cation $(L-H)_d^+$ may also be an abstracting moiety such as a silver, carbonium, tropylium, carbenium, ferrocenium species and mixtures thereof, preferably carbonium or ferrocenium species. Most preferably $(L-H)_d^+$ is triphenylcarbonium.

The anion component $A^{d-}$ includes those having the formula $[M^{k+}Q_n]^{d-}$ wherein k is an integer from 1 to 3; n is an integer from 2 to 6; n—k=d; M is an element selected from Group 13 of the Periodic Table of the Elements, preferably boron or aluminum, and Q is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms; more preferably each Q is a fluorinated aryl group, and most preferably each Q is a pentafluoroaryl group. Non-limiting examples of suitable $A^{d-}$ species also include diboron compounds as disclosed in U.S. Pat. No. 5,447,895, fully incorporated herein by reference.

Most preferably, the ionic stoichiometric activator $(L-H)_d^+ (A^{d-})$ is N,N-dimethylanilinium tetra(perfluorophenyl)borate or triphenylcarbenium tetra(perfluorophenyl)borate.

In one aspect, an activation method using ionizing ionic compounds not containing an active proton but capable of producing a catalyst precursor compound cation and its non-coordinating anion are also contemplated, and are described in EP-A-0 426 637, EP-A-0 573 403 and U.S. Pat. No. 5,387,568, which are all herein fully incorporated by reference.

The mole ratio of the metal or metalloid of the activator component to the metals of the supported linked metallocene catalyst complex are in the range of between 0.3:1 to 1000:1, preferably 20:1 to 800:1, and most preferably 50:1 to 500:1. Where the activator is an ionizing activator such as those based on the anion tetrakis(pentafluorophenyl) boron, the mole ratio of the metal or metalloid of the activator component to the metal component of the metallocene catalyst is preferably in the range of between 0.3:1 to 3:1.

Where an unsupported metallocene catalyst system is utilized, the mole ratio of the metal or metalloid of the activator component to the metals of the linked metallocene catalyst complex is in the range of between 0.3:1 to 10,000:1, preferably 100:1 to 5000:1, and most preferably 500:1 to 2000:1.

Support Materials and Methods for Supporting

The above linked metallocene catalyst complexes may be combined with one or more support materials or carriers using one of the support methods known in the art or as described below. In one embodiment, a method of the invention uses a polymerization catalyst system in supported form, for example deposited on, bonded to, contacted with, or incorporated within, adsorbed or absorbed in, or on, a support or carrier.

The terms "support" or "carrier" are used interchangeably and are any support material, preferably a porous support material, for example, talc, inorganic oxides and inorganic chlorides. Other carriers include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred carriers are inorganic oxides that include those Group 2, 3, 4, 5, 13 or 14 metal oxides. The preferred supports include silica, alumina, silica-alumina, magnesium chloride, and mixtures thereof. Other useful supports include magnesia, titania, zirconia, montmorillonite (EP-B1 0 511 665), zeolites, and the like. Also, combinations of these support materials may be used, for example, silica-chromium, silica-alumina, silica-titania and the like.

It is preferred that the carrier, most preferably an inorganic oxide, has a surface area in the range of from about 10 to about 700 $m^2/g$, pore volume in the range of from about 0.1 to about 4.0 cc/g and average particle size in the range of from about 5 to about 500 $\mu$m. More preferably, the surface area of the carrier is in the range of from about 50 to about 500 $m^2/g$, pore volume of from about 0.5 to about 3.5 cc/g and average particle size of from about 10 to about 200 $\mu$m. Most preferably the surface area of the carrier is in the range is from about 100 to about 400 $m^2/g$, pore volume from about 0.8 to about 3.0 cc/g and average particle size is from about 5 to about 100 $\mu$m. The average pore size of the carrier of the invention typically has pore size in the range of from 10 to 1000 Å, preferably 50 to about 500 Å, and most preferably 75 to about 350 Å.

Examples of supporting the metallocene catalyst systems of the invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664 and U.S. application Ser. Nos. 271,598 filed Jul. 7, 1994 and 788,736 filed Jan. 23, 1997 and PCT publications WO 95/32995, WO 95/14044, WO 96/06187 and WO 97/02297 all of which are herein fully incorporated by reference.

In one embodiment, the linked metallocene complexes of the invention may be deposited on the same or separate supports together with an activator, or the activator may be used in an unsupported form, or may be deposited on a support different from the supported metallocene catalyst compounds of the invention, or any combination thereof.

Procedures for measuring the total pore volume of a porous support are well known in the art. Details of one of these procedures is discussed in Volume 1, *Experimental Methods in Catalytic Research* (Academic Press, 1968) (specifically see pages 67–96). This preferred procedure involves the use of a classical BET apparatus for nitrogen absorption. Another method well known in the art is described in Innes, *Total Porosity and Particle Density of Fluid Catalysts By Liquid Titration,* Vol. 28, No. 3, Analytical Chemistry 332–334 (March, 1956).

In one embodiment the linked metallocene polymerization catalyst complex is used in an unsupported form, preferably in a liquid form such as described in U.S. Pat. Nos. 5,317,036 and 5,693,727 and European publication EP-A-0 593 083, all of which are herein incorporated by reference. The polymerization catalyst in liquid form can be fed to a reactor as described in PCT publication WO 97/46599, which is fully incorporated herein by reference.

In one embodiment, the linked metallocene polymerization catalyst complexes of the invention can be combined with a carboxylic acid salt of a metal ester, for example aluminum carboxylates such as aluminum mono, di- and tri-stearates, aluminum octoates, oleates and cyclohexylbutyrates, as described in U.S. application Ser. No. 09/113,216, filed Jul. 10, 1998.

Polymerization Process

The linked metallocene catalyst complexes and catalyst systems of the invention described above are suitable for use in any polymerization process over a wide range of temperatures and pressures. The temperatures may be in the range of from −60° C. to about 280° C., preferably from 50° C. to about 200° C. In one embodiment, the polymerization process is conducted above 70° C. and preferably above 80° C. The pressures employed may be in the range from 1 atmosphere to about 500 atmospheres or higher.

Polymerization processes include solution, gas phase, slurry phase and a high pressure process or a combination thereof. Particularly preferred are a gas phase or slurry phase polymerization process of one or more olefins at least one of which is ethylene.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, butene-1, pentene-1,4-methyl-pentene-1, hexene-1, octene-1 and decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligand metallocene-type catalysts as described in U.S. Pat. Nos. 5,296,434 and 5,278,264, both of which are herein incorporated by reference.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In a preferred embodiment, the reactor utilized in the present invention is capable and the process of the invention is producing greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In an embodiment which are herein fully incorporated by reference.

Polymer Product of the Invention

The polymers and blends including the polymers produced in the process of the invention can be used in a wide variety of products and end-use applications. The polymers produced by the process of the invention include linear low density polyethylene, elastomers, plastomers, high density polyethylenes, low density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc to about 0.930 g/cc.

The melt strength of the polymers produced using the catalyst of the invention are greater than 6 cN, preferably greater than 7 cN, and most preferably 8 cN or higher. For purposes of this patent application and appended claims melt strength is measured with an Instron capillary rheometer in conjunction with the Goettfert Rheotens melt strength apparatus. A polymer melt strand extruded from the capillary die is gripped between two counter-rotating wheels on the apparatus. The take-up speed is increased at a constant acceleration of 24 mm/sec$^2$, which is controlled by the Acceleration Programmer (Model 45917, at a setting of 12). The maximum pulling force (in the unit of cN) achieved before the strand breaks or starts to show draw-resonance is determined as the melt strength. The temperature of the rheometer is set at 190° C. The capillary die has a length of one inch (2.54 cm) and a diameter of 0.06" (0.1 5 cm). The polymer melt is extruded from the die at a speed of 3 inch/min (7.62 cm/min). The distance between the die exit and the wheel contact point should be 3.94 inches (100 mm).

The polymers produced by the process of the invention typically have a molecular weight distribution, a weight average molecular weight to number average molecular weight ($M_w/M_n$) of greater than 1.5 to about 15, particularly greater than 2 to about 10, more preferably greater than about 2.5 to less than about 8, and most preferably from 3.0 to 8.

In one embodiment, the polymers of the present invention have a $M_z/M_w$ of greater than or equal to 3, preferably greater than 3. $M_z$ is the z-average molecular weight. In another preferred embodiment, the polymers of the invention have a $M_z/M_w$ of greater than or equal to 3.0 to about 4. In yet another preferred embodiment, the $M_z/M_w$ is in the range greater than 3 to less than 4.

Also, the polymers of the invention may have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993, which is fully incorporated herein by reference.

The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%. In another embodiment, the polymers have a CDBI less than 50%, more preferably less than 40%, and most preferably less than 30%.

The polymers of the present invention in one embodiment have a melt index (MI) or ($I_2$) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min.

The polymers of the invention in an embodiment have a melt index ratio ($I_{21}/I_2$) ($I_{21}$ is measured by ASTM-D-1238-

F) of from 30 to less than 200, more preferably from about 35 to less than 100, and most preferably from 40 to 95.

The polymers of the invention in a preferred embodiment have a melt index ratio ($I_{21}/I_2$) of from preferably greater than 30, more preferably greater than 35, even more preferably greater that 40, still even more preferably greater than 50 and most preferably greater than 65.

The polymers of the invention may be blended and/or coextruded with any other polymer. Non-limiting examples of other polymers include linear low density polyethylenes produced via conventional Ziegler-Natta and/or metallocene catalysis, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc.

When an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed. Moreover, the upper and lower values of any two (or more) ranges given for a specific parameter are to be understood as also disclosing the ranges formed by combining the lower value of a first range with the upper value of a second range and vice versa.

EXAMPLES

In order to provide a better understanding of the present invention including representative advantages thereof, the following examples are offered.

All reactions were performed under nitrogen in a drybox or connected to Schlenk lines unless stated otherwise. n-Butyl lithium (2.5M in hexanes), and solvents were purchased from Aldrich, Milwaukee, Wis. 30 wt % methylaluminoxane in toluene was purchased from Albermarle, Baton Rouge, La., and was used as received. Triisobutylaluminum was puchased from Akzo Nobel, Houston, Tex., and was used as recieved. $Zr(NMe_2)_4$ was prepared by the method described by Jordan et al (Organometallics 1995, 14, 5.) or was purchased from Strem Chemicals, Newburyport, Mass. $Hf(NMe_2)_4$ was purchased from Strem Chemicals. $ClCH_2CH_2CH_2SiCl_2(CH_3)$ & $n\text{-butyl}_3SnCl$ were purchased from Gelest, Tullytown, Pa.

Example 1

Synthesis of $ClCH_2CH_2CH_2(CH_3)Si(CpH)(CpMe_4H)$ 64 mls of n-butyl lithium (2.5M in hexanes) was added dropwise to a solution of tetramethylcyclopentadiene at −35° C. in tetrahydrofuran (1 liter, 2 liter flask). An exothermic reaction takes place yielding a thick white precipitate. 30.63 grams of $ClCH_2CH_2CH_2SiCl_2(CH_3)$ was added to the slurry of lithium tetramethylcyclopentadienyl. Over a period of several hours the slurry yields a colorless solution. 11.5 grams of lithium cyclopentadienyl was added to the solution and allowed to stir for two hours. The solvent was removed. Pentane was added and the resulting slurry was filtered yielding 13.5 grams of lithium chloride. The pentane solution was dried and quantitative yields of $ClCH_2CH_2CH_2(CH_3)Si(CpH)(CpMe_4H)$ was isolated as a golden oil.

Example 2

Synthesis of $ClCH_2CH_2CH_2(CH_3)Si(Cp)(CpMe_4)Zr(NMe_2)_2$ $ClCH_2CH_2CH_2(CH_3)Si(CpH)(CpMe_4H)$. (10.0 grams) was combined with $Zr(NMe_2)_4$ (8.73 grams) in toluene (200 mls). The solution was stirred at 100° C. for fifteen minutes. The solvent was removed yielding a yellow solid. Pentane cooled to −35° C. and was used to rinse the solid. 11.0 grams of product was obtained. $^1H$ NMR ($CD_2Cl_2$); 0.624 (s), 1.72 (m), 1.89 (s), 1.92 (s), 1.98 (s), 2.02 (2), 2.63 (s), 2.66 (s), 3.55(t), 5.64 (m), 6.49 (m).

Example 3

Synthesis of $HIndCH_2CH_2CH_2(CH_3)Si(Cp)(CpMe_4)Zr(NMe_2)_2$ 15.2 grams of $ClCH_2CH_2CH_2(CH_3)Si(Cp)(CpMe_4)Zr(NMe_2)_2$ was combined with 3.83 grams of lithium indenide at −35° C. in tetrahydrofuran (150 mls) The solution was then heated to 60° C. for 30 minutes. The solvent was removed, and pentane was added. The pentane slurry was filtered removing lithium chloride. Evaporation of the pentane solution yielded a red sticky product. $^1H$ NMR (THF-d8); δ0.671 (overlapping singlets), 0.705 ((overlapping singlets), 1,3 (m) 1.96–2.06(overlapping singlets), 2.72–2.75(overlapping singlets), 3.30(s), 2.07(s), 5.69 (m), 5.73 (m), 6.28, 6.55, 6.75, 7.12 (m), 7.38 (m).

Example 4

Synthesis of $CpZr(Cl)_2IndCH_2CH_2CH_2(CH_3)Si(Cp)(CpMe_4)Zr(NMe_2)_2$ 2.0 grams of $HIndCH_2CH_2CH_2(CH_3)Si(Cp)(CpMe_4)Zr(NMe_2)_2$ was cooled to −35° C. in diethyl ether. 1.35 mls of n-butyl lithium (2.5M in hexanes) was added to the solution dropwise. Cyclopentadienyl zirconium trichloride (0.93 grams) was added to the solution and the resulting slurry was allowed to warm to room temperature and stir overnight. The solvent was removed, and the product (1.7 grams) was extracted with pentane. $^1H$ NMR ($CD_2Cl_2$); δ0.635 (overlapping singlets), 1.3 (m), 1.33 (m), 1.8–1.99 (overlapping singlets), 2.69 (s), 2.96 (m), 3.15 (m), 5.53 (m), 5.67 (m), 6.01 (s), 6.15 (d), 6.47 (m), 6.68 (d), 7.28 (m), 7.63 (m).

Example 5

Synthesis of $CpZr(Cl)_2IndCH_2CH_2CH_2(CH_3)Si(Cp)(CpMe_4)ZrCl_2$ $CpZr(Cl)_2IndCH_2CH_2CH_2(CH_3)Si(Cp)(CpMe_4)Zr(NMe_2)_2$ was dissolved in dichloromethane. Trimethylsilylchloride in large excess was added to the solution and stirred for thirty minutes. Pentane was added to precipitate the product which was filtered and dried under vacuum (1.3 grams). $^1$H NMR (CD$_2$Cl$_2$); δ0.789 (s), 0.800 (s), 1.33 (m), 1.82(s), 1.83(s), 1.95(s), 1.98(s), 2.99 (m), 3.19 (m), 5.57 (m), 5.69 (m), 6.15 (s), 6.50 (d), 6.69 (d), 6.93 (m), 7.26 (m), 7.64 (t). Note: residual TMSNMe$_2$ @0.428 (s), 1.694 (s).

Example 6

Synthesis of ClCH$_2$CH$_2$CH$_2$(CH$_3$)Si((3,4)PrCpH)$_2$ (isomers)

38.9 grams of ClCH$_2$CH$_2$CH$_2$SiCl$_2$(CH$_3$) was added to a solution of lithium n-propylcyclopentadienyl (46.3 grams) in tetrahydrofuran at −70° C. After one hour the slurry was allowed to warm to room temperature. After two hours the solvent was removed. Pentane was added and the resulting slurry was filtered yielding 17 grams of lithium chloride. The pentane solution was dried and quantitative yields of ClCH$_2$CH$_2$CH$_2$(CH$_3$)Si(PrCpH)$_2$ was isolated as a reddish brown oil.

Example 7

Synthesis of ClCH$_2$CH$_2$CH$_2$(CH$_3$)Si((3,4)PrCp)$_2$Hf (NMe$_2$)$_2$ (isomers)

ClCH$_2$CH$_2$CH$_2$(CH$_3$)Si((3,4)PrCpH)$_2$ (30.0 grams) was combined with Hf(NMe$_2$)$_4$ (31.7 grams) in toluene (200 mls). The solution was stirred at 60° C. for three hours. The solvent was removed and pentane was added from which a slight amount of tan powder was removed. The pentane solution was dried under vacuum yielding an oil (40.87 grams) which was further subjected to 70° C. under vacuum for three hours.

Example 8

Synthesis of LiIndCH$_2$CH$_2$CH$_2$(CH$_3$)Si((3,4)PrCp)$_2$Hf(NMe$_2$)$_2$ (isomers)

40.87 grams of ClCH$_2$CH$_2$CH$_2$(CH$_3$)Si((3,4)PrCp)$_2$Hf (NMe$_2$)$_2$ was combined with 8.32 grams of lithium indenide at −35° C. in tetrahydrofuran (150 mls). The solution was then heated to 60° C. for 3 hours. The solvent was removed, and ether was added. The ether slurry was filtered removing lithium chloride. The filtered solution was reacted with 225.5 mls of n-butyl lithium (2.5 M in hexanes). The solution was concentrated, and pentane was added precipitating an oil. The oil was washed with 400 mls of pentane yielding an orange solid.

Example 9

Synthesis of Cl$_2$Zr[IndCH$_2$CH$_2$CH$_2$(CH$_3$)Si((3,4)PrCp)$_2$HfCl$_2$]$_2$ 10 grams of LiIndCH$_2$CH$_2$CH$_2$(CH$_3$)Si((3,4)PrCp)$_2$Hf(NMe$_2$)$_2$, was combined with 1.7 grams of ZrCl$_4$ in ether at −35° C. The solution was warmed to room temperature and stirred overnight. The solvent was removed, and pentane was added. The pentane slurry was filtered, and the resulting pentane solution was dried under vacuum. The resulting orange solid was dissolved into toluene and reacted with a large excess of trimethylsilylchloride overnight at room temperature. The solvent was removed and the addition of pentane yielded an orange slurry which was filtered. The orange yellow solid was dried under vacuum.

Example 10

Synthesis of ClCH$_2$CH$_2$CH$_2$CH$_2$CpH 11.4 grams of cyclopentadienyl lithium was added to a solution of 1,4-bromochlorobutane (27.2 grams) at −70° C. The solution was allowed to warm to room temperature overnight. The solvent was removed, and pentane was added. The pentane slurry was filtered to remove LiBr. The filtrate was dried under vacuum yielding a golden oil. The oil was distilled under vacuum (pot temp. 70° C., distillation temp. 40–50° C., 500 mm Hg).

Example 11

Synthesis of (ClCH$_2$CH$_2$CH$_2$CH$_2$Cp)$_2$Hf(NMe$_2$)$_2$

ClCH$_2$CH$_2$CH$_2$CH$_2$CpH (24.0 grams) was combined with Hf(NMe$_2$)$_4$ (25.0 grams) in toluene (200 mls). The solution was stirred at 60° C. for one hour. The solvent was removed under vacuum yielding an oil with solidified after several days. $^1$H NMR (CD$_2$Cl$_2$); δ1.61 (m), 1.68 (m), 2.41 (t), 2.72 (s), 3.47 (t), 5.78 (m), 5.91 (m).

Example 12

Synthesis of (HIndCH$_2$CH$_2$CH$_2$CH$_2$Cp)$_2$Hf(NMe$_2$)$_2$ 7.7 grams of (ClCH$_2$CH$_2$CH$_2$CH$_2$Cp)$_2$Hf(NMe$_2$)$_2$ was combined with 3.25 grams of lithium indenide in tetrahydrofuran (150 mls). The solution was then heated to 60° C. for 1 hour. The solvent was removed, and pentane was added. The pentane slurry was filtered removing lithium chloride. The resulting pentane solution was evaporated yielding 5.68 grams of a golden oil. $^1$H NMR (CD$_2$Cl$_2$); δ1.67 (m), 2.48 (m), 2.73 (s), 3.26 (s), 3.34 (s), 5.78 (m), 5.91 (m), 6.15 (s), 7.11–7.40 (m).

Example 13

Synthesis of (LiIndCH$_2$CH$_2$CH$_2$CH$_2$Cp)$_2$Hf(NMe$_2$)$_2$ 5.68 grams of (HIndCH$_2$CH$_2$CH$_2$CH$_2$Cp)$_2$Hf(NMe$_2$)$_2$, was combined with 5.82 mls of n-butyl lithium (2.5 M in hexanes). Pentane was added, and the pentane slurry was filtered yielding 4.90 grams of yellow powder. $^1$H NMR (THF-d8); δ1.67 (m), 1.73 (m), 2.48 (t), 2.78(s), 2.87(t), 5.72(d), 5.79(m), 5.96 (m), 6.38 (d), 6.42, (m), 7.30 (m).

Example 14

Syntheses of (n-bu)$_3$Sn(MeInd)

1(3)-methylindene (20 grams) was dissolved into diethyl ether. The solution was cooled to −35° C. 59.2 mls of n-butyl lithium (2.5 M in hexanes) was added dropwise. 50.1 grams of n-butyl$_3$SnCl was added slowly to the solution of lithium 1-methylindenyl. The diethyl ether solvent was removed under vacuum. Pentane was added, and the slurry was filtered. Removal of the pentane under vacuum yielded 58.3 gram of product (yellow oil).

Example 15

Synthesis of 1-MeIndZrCl$_3$ 32.4 grams of ZrCl$_4$ was placed in a toluene slurry (300 mls). 58.3 grams of (n-bu)$_3$Sn(MeInd) was added dropwise. The reaction was stirred overnight. The orange powder in the slurry was filtered, rinsed with pentane, and dried under vacuum.

Example 16

Synthesis of (Cl$_2$Zr(1-MeInd)Ind-1-CH$_2$CH$_2$CH$_2$CH$_2$Cp)$_2$HfCl$_2$ (isomers)

4.9 grams of (LiIndCH$_2$CH$_2$CH$_2$CH$_2$Cp)$_2$Hf(NMe$_2$)$_2$, was combined with 4.27 grams of 1-MeIndZrCl$_3$ in toluene.

The resulting slurry was stirred overnight. The toluene slurry was filtered through celite, and the solution was reacted with excess TMSCl (several hours room temperature). The solution was concentrated, and pentane was added yielding an orange powder.

Example 17

Preparation of Catalyst A 0.024 grams of $CpZr(Cl)_2IndCH_2CH_2CH_2(CH_3)Si(Cp)$ $(CpMe_4)ZrCl_2$ was combined with 1.0 grams of supported methylaluminoxane yielding a toluene slurry. After fifteen minutes the slurry was filtered, rinsed with toluene, and the resulting supported catalyst was dried under vacuum.

Example 18

Preparation of Catalyst B 0.630 grams of $CpZr(Cl)_2IndCH_2CH_2CH_2(CH_3)Si(Cp)$ $(CpMe_4)ZrCl_2$ was combined with 42.0 grams of supported methylaluminoxane yielding a toluene slurry. After thirty minutes the slurry was filtered, rinsed with pentane, and the resulting supported catalyst was dried under vacuum overnight.

Example 19

Preparation of Catalyst C 2.0 grams of $Cl_2Zr[IndCH_2CH_2CH_2(CH_3)Si((3,4)PrCp)_2 HfCl_2]_2$ was combined with 100 grams of supported methylaluminoxane yielding a toluene slurry. After thirty minutes the slurry was filtered, rinsed with pentane, and the resulting supported catalyst was dried under vacuum overnight.

Example 20

Preparation of Catalyst D 1.06 grams of $(Cl_2Zr(1-MeInd)Ind-1-CH_2CH_2CH_2CH_2Cp)_2HfCl_2$ was combined with 42 grams of supported methylaluminoxane yielding a toluene slurry. After thirty minutes the slurry was filtered, rinsed with pentane, and the resulting supported catalyst was dried under vacuum overnight.

Example 21

Ethylene-Hexene Polymerization using Catalyst A

Polymerizations were conducted in a stainless steel, 1-liter Zipperclave autoclave reactor. The reactor was equipped with water jacket for heating and cooling. Injections were performed via a high pressure nitrogen injection. (400 mls isobutane, 10 mls of hexene, and 100 µls triisobutylaluminum) Before polymerizations the reactor was purged with nitrogen for several hours at 100° C. Upon injection of catalyst ethylene was fed continuously on demand keeping the reactor pressure constant (130 psig ethylene) while maintaining the reaction temperature at 85° C. After the allotted time the reaction was stopped by cooling and venting the pressure and exposing the contents of the reactor to air. The liquid components were evaporated and the poly(ethylene-co-hexene-1) resin was dried under a $N_2$ purge. Weight average molecular weight (Mw), number average molecular weight (Mn) and their ratio Mw/Mn were obtained by GPC gel permeation chromotagraphy. Hexene wt % incorporation was obtained from $^1H$ NMR data.

The above procedure was performed using 25 mgs of Catalyst A. After 40 minutes the reaction was stopped. No reactor fouling was observed. Run 1; 32.7 grams of polymer resin (1962 g pol./g cat. h); Mw=59,400, Mn=31800, Mw/Mn=1.86; Hexene wt %=3.7. Run 2; 27.6 grams of polymer resin (1655 g pol./g cat. h); Mw=62,100, Mn=34,200, Mw/Mn=1.81; Hexene wt %=3.8.

Example 22

Ethylene-Hexene Polymerization Procedure Utilizing Catalyst B

Polymerizations were carried out in the gas phase using an 8 inch fluid bed reactor. Before polymerization, a polyethylene pre-bed was loaded into the reactor. It was then purged with dry nitrogen. Then the catalyst (in the form of dry powder), ethylene monomer, co-monomer (1-hexene), hydrogen and nitrogen gases were continuously injected into the reactor, along with the continuous injection of the indicated organometallic compound which was injected through a separate injection port. The gaseous composition was continuously monitored by in-line GC. Polymerization was carried out at 85° C. When the reactor bed weight reached a certain level, polyethylene product was discharged through a discharge port.

Example 22A

Polymerization was carried out at 85° C., 220 psia ethylene partial pressure, 350 psig reactor pressure, hexene/ethylene mole ratio of 0.014 and hydrogen/ethylene ratio of 0.0013. About 42 lbs of product was made. The activity of the catalyst B corresponds to 5 ppm Hf and 2.3 ppm Zr in the product. Product had a melt index of 3.8 (gm/10 min) and melt flow ratio of 27 and density of 0.923 g/cc. Average particle size was 0.019 in and the bulk density, 26.6 lb/cu.ft.

Example 22B

Polymerization conditions were same as in Example 22A but for the hydrogen ratio. No hydrogen was fed to the reactor. Based on the hydrogen generated in the reaction, hydrogen/ethylene ratio was found to be 0.0003. About 43 lbs of product was made. The activity of the catalyst corresponds to 4.5 ppm Hf and 1.6 ppm Zr in the product. Product had a melt index of 0.3 (gm/10 min) and melt flow ratio of 58 and density of 0.918 g/cc. Average particle size was 0.019 in and the bulk density, 29 lb/cu.ft.

Example 23

Ethylene-Hexene Polymerization Procedure Utilizing Catalyst D

Polymerization were carried out in the gas phase using a gas phase fluidized bed reactor which comprised an 18 inch (45.7 cm) diameter, schedule 60 reactor having an internal diameter of 16.5 inches (41.9 cm). The ethylene concentration was controlled to maintain a constant ethylene partial pressure. The solid supported Catalyst D was injected directly into the fluidized bed using purified nitrogen. The reactor was operated at a total pressure of 300 psig (2069 kPa), a reactor temperature of 85° C. and a superficial gas velocity of 2.25 ft/sec (68.6 cm/sec) was used to achieve fluidization of the granules. To maintain a constant reactor temperature, the temperature of the recycle gas is continuously adjusted up or down to accommodate any changes in the rate of heat generation due to the polymerization. The fluidized bed was maintained at a constant height by withdrawing a portion of the bed at a rate equal to the rate of formation of particulate product. Run and product data for Example 23 and for Comparative Example 24 appear in Table 1.

Comparative Example 24

Polymerization Utilizing $Cl_2Zr(1\text{-MeInd})_2$ and $(CH_3CH_2CH_2Cp)_2HfCl_2$ Mixed Catalyst System Preparation of rac/meso bis(1-methylindenyl)zirconium dichloride. To a light orange solution of lithium(1-methylindenide) (4.67 g, 34.3 mmoles, 2.00 equiv.) in 1,2-dimethoxyethane (80 mL) at −35° C. was added $ZrCl_4$ (4.00 g, 17.2 mmoles, 1.00 equiv.) in portions. The reaction initially turned clear, dark green, then quickly became cloudy with precipitate. The mixture was allowed to warm to room temperature and stir overnight. After stirring 18 hours, the cloudy orange mixture was evaporated in vacuo, leaving orange-yellow solid. The solid was extracted with dichloromethane (3×25 mL) and the resulting mixture was filtered to give a bright yellow solution and pink solid. The yellow solution was evaporated in vacuo, leaving a bright yellow powder. Yield 7.05 g (98%). The isolated product is a 1:1 mixture of rac and meso isomers by $^1H$ NMR. $^1H$ NMR($CD_2Cl_2$): δ2.36 (s, 6H, Me), 2.42 (s, 6H, Me), 5.76 (d, 2H, $C_5$ ring-H), 5.94 (d, 2H, $C_5$ ring-H), 6.10 (d, 2H, $C_5$ ring-H), 6.36 (d, 2H, $C_5$ ring-H), 7.28 (m, 8H, $C_6$ ring-H), 7.45–7.63 (m, 8H, $C_6$ ring-H).

Preparation of bis(propylcyclopentadienyl)hafnium dichloride. $HfCl_4$ (30.00 g, 93.7 mmoles, 1.00 equiv.) was added in portions to cold (−35° C.) ether (400 mL) to give a white suspension. The suspension was stirred briefly and then recooled to −35° C. Lithium (propylcyclopentadienide) (21.38 g, 187 mmoles, 2.00 equiv.) was added to the cold suspension in portions, giving a light manila-brown mixture. The mixture was allowed to warm to room temperature and stir overnight. After stirring 17 hours, the brown mixture was filtered to give a straw yellow solution and brown solid. The solid was washed with ether, and the combined ether solutions were concentrated to approximately 100 mL in vacuo. Light, straw-yellow crystals were filtered from the cold, concentrated solution and dried in vacuo. Yield 32.69 g (75%). The mother liquors were concentrated again to approximately 20 mL, and a second crop of crystals was isolated by filtration and dried in vacuo. The total yield was 33.59 g (77%). $^1H$ NMR($CD_2Cl_2$): δ0.92 (t, 6H, $CH_2CH_2$ $CH_3$), 1.56 (m, 4H, $CH_2CH_2CH_3$), 2.60 (t, 4H, $\overline{CH_2}CH_2CH_3$), 6.10 (m, 4H, ring-$\overline{H}$), 6.21 (m, 4H, ring-H).

Preparation of supported rac/meso bis(1-methylindenyl) zirconium dichloride. 37.27 g of 30 wt % MAO in toluene and 39.00 g toluene were combined to give a clear, colorless solution. The solution was stirred 15 min., then 0.675 g rac/meso bis(1-methylindenyl)zirconium dichloride was added. The solution darkened to murky red initially, then soon lightened to clear orange. The reaction was stirred 15 min., then 30.00 g Davison 948 silica (50 μ, dried at 600° C.) was added and the resulting thick mixture was stirred by hand using a spatula for 10 min. The yellow-orange mixture was dried 20 hours in vacuo to give 42.41 g (101%) yellow-orange, free-flowing solid.

Preparation of supported bis(propylcyclopentadienyl) hafnium dichloride. Bis(propylcyclopentadienyl)hafnium dichloride was supported in a manner similar to rac/meso bis(1-methylindenyl)zirconium dichloride using 37.37 g of 30 wt % MAO and 0.747 g bis(propylcyclopentadienyl) hafnium dichloride, which yielded 42.13 g (100%) white, free-flowing solid.

Preparation of supported mixed bis (propylcyclopentadienyl)hafnium dichloride and rac/meso bis(1-methylindenyl)zirconium dichloride. Mixed bis (propylcyclopentadienyl)hafnium dichloride and rac/meso bis(1-methylindenyl)zirconium dichloride were supported in a manner similar to rac/meso bis(1-methylindenyl) zirconium dichloride using 0.299 g bis (propylcyclopentadienyl)hafnium dichloride, 0.405 g rac /meso bis(1-methylindenyl)zirconium dichloride and 37.31 g of 30 wt % MAO, which yielded 42.22 g (101%) manila-colored, free-flowing solid.

Polymerization utilizing the supported mixed bis (propylcyclopentadienyl)hafnium dichloride and rac/meso bis(1-methylindenyl)zirconium dichloride was conducted according with Example 23. Run and product data for Example 23 and for Comparative Example 24 appear in Table 1.

TABLE 1

| Example Number | Comp. Example 24 | Catalyst D |
|---|---|---|
| H2 conc. (molppm) | 34 | 44 |
| Hydrogen flow (sccm) | 0.15 | 0.00 |
| Comonomer conc. (mol %) | 0.95 | 1.67 |
| C2 conc. (mol %) | 35.0 | 35.0 |
| Comonomer/C2 Flow Ratio | 0.114 | 0.15 |
| C2 flow (g/hr) | 634 | 459 |
| H2/C2 Ratio | 1.0 | 1.3 |
| Comonomer/C2 Ratio | 0.027 | 0.048 |
| Rx. Pressure (psig) | 300 | 300 |
| Reactor Temp (F) | 175 | 175 |
| Avg. Bedweight (g) | 1956 | 1938 |
| Production (g/hr) | 471 | 278 |
| Residence Time (hr) | 4.2 | 7.0 |
| C2 Utilization (gC2/gC2 poly) | 1.35 | 1.65 |
| Avg Velocity (ft/s) | 1.59 | 1.67 |
| Catalyst Timer (minutes) | 45.0 | 30.0 |
| Bulk Density | 0.3855 | 0.4183 |
| Product Data | | |
| Melt Index (MI) | 1.14 | 1.74 |
| HLMI | 31.3 | 39.8 |
| HLMI/MI Ratio | 27.5 | 22.9 |
| Density (g/cc) | 0.9185 | 0.9192 |
| Mn | 33370 | 20580 |
| Mw | 147200 | 103900 |
| Mz | 567000 | 128000 |
| Mw/Mn | 4.41 | 5.05 |
| Mz/Mw | 3.85 | 1.23 |
| Melt strength (cN) | 8.7 | 27 |

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

We claim:

1. A metallocene complex comprising:
   (a) at least one bridged metallocene component containing a first bridging group;
   (b) an unbridged metallocene component having a first aromatic ring system and a second aromatic ring system, wherein the first aromatic ring system of the unbridged metallocene is linked to the first bridging group; and
   (c) a second bridged metallocene component containing a second bridging group, wherein the second aromatic ring system of the unbridged metallocene is linked to the second bridging group.

2. The metallocene complex of claim 1 represented by the formula:

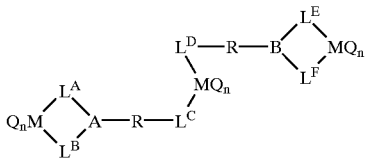

wherein each M is a metal atom;
each Q is independently a leaving group;
n is 0, 1 or 2;
$L^A, L^B, L^C, L^D, L^E$ and $L^F$ are each aromatic ring systems composed of atoms selected from Groups 13 to 16 of the Periodic Table of Elements;
A and B are bridging groups each comprising at least one Group 13 to 16 atom; and
each R is a linking group comprising a substituted or unsubstituted hydrocarbyl group.

3. The metallocene complex of claim 2 wherein $L^A$, $L^B$, $L^C$, $L^D$, $L^E$ and $L^F$ each comprise a unsubstituted or substituted cyclopentadienyl ligand or cyclopentadienyl group containing ligand, each M is a Group 4 atom, A and B independently comprises an atom selected from Si, Ge, and C, R is an alkyl group, and each Q is independently a halogen.

4. The metallocene complex of claim 3 wherein $L^A$ is the same as $L^E$, $L^B$ is the same as $L^F$, $L^C$ is the same as $L^D$, the Group 4 atom connected to $L^A$ and $L^B$ is the same as the Group 4 atom connected to $L^E$ and $L^F$.

5. The metallocene complex of claim 1 wherein metallocene components comprise at least one good comonomer incorporator and at least one poor comonomer incorporator.

6. A metallocene complex comprising a first unbridged metallocene component containing a first metal atom bonded to a ligand $L^A$ and a ligand $L^B$ and a second unbridged metallocene component containing a second metal bonded to a ligand $L^C$ and a ligand $L^D$, wherein $L^A$, $L^B$, $L^C$ and $L^D$ are unsubstituted or substituted cyclopentadienyl ligands or cyclopentadienyl group containing ligands, and wherein the ligand $L^B$ is linked to the ligand $L^C$ by a first linking group; and a third unbridged metallocene structure having a ligand $L^E$ and a ligand $L^F$, wherein $L^E$ and $L^F$ are unsubstituted or substituted cyclopentadienyl ligands or cyclopentadienyl group containing ligands, and wherein $L^E$ is linked to $L^D$ by a second linking group.

7. The metallocene complex of claim 6 represented by the formula:

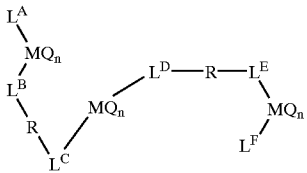

wherein each M is a metal atom;
each Q is independently a leaving group;
n is 0, 1 or 2;
$L^A, L^B, L^C, L^D, L^E$ and $L^F$ are each aromatic ring systems composed of atoms selected from Groups 13 to 16 of the Periodic Table of Elements; and
each R is a linking group comprising a substituted or unsubstituted hydrocarbyl group.

8. The metallocene complex of claim 7 wherein $L^A$, $L^B$, $L^C$, $L^D$, $L^E$ and $L^F$ each comprise a unsubstituted or substituted cyclopentadienyl ligand or cyclopentadienyl group containing ligand, each M is a Group 4 atom, R is an alkyl group, and each Q is independently a halogen.

9. The metallocene complex of claim 8 wherein $L^A$ is the same as $L^F$, $L^B$ is the same as $L^E$, $L^C$ is the same as $L^D$, Group 4 atom connected to $L^A$ and $L^B$ is the same as the Group 4 atom connected to $L^E$ and $L^F$.

10. The metallocene complex of claim 6 wherein metallocene components comprise at least one good comonomer incorporator and at least one poor comonomer incorporator.

11. A metallocene complex represented by the following formula:

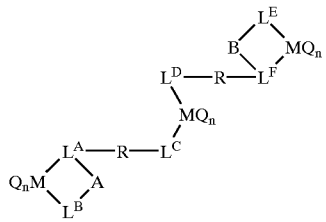

wherein each M is a metal atom;
each Q is independently a leaving group;
n is 0, 1 or 2;
$L^A, L^B, L^C, L^D, L^E$ and $L^F$ are each aromatic ring systems composed of atoms selected from Groups 13 to 16 of the Periodic Table of Elements;
A and B are bridging groups each comprising at least one Group 13 to 16 atom; and
each R is a linking group comprising a substituted or unsubstituted hydrocarbyl group.

12. The metallocene complex of claim 11 wherein $L^A$, $L^B$, $L^C$, $L^D$, $L^E$ and $L^F$ each comprise a unsubstituted or substituted cyclopentadienyl ligand or cyclopentadienyl group containing ligand, each M is a Group 4 atom, R is an alkyl group, and each Q is independently a halogen.

13. The metallocene complex of claim 11 wherein $L^A$ is the same as $L^F$, $L^B$ is the same as $L^E$, $L^C$ is the same as $L^D$, the Group 4 atom connected to $L^A$ and $L^B$ is the same as the Group 4 atom connected to $L^E$ and $L^F$.

14. The metallocene complex of claim 11 wherein metallocene components comprise at least one comonomer incorporator and at least one poor comonomer incorporator.

15. A method for preparing a catalyst complex comprising:
(a) reacting X—R—A—X-Cp1, wherein X is a halogen, each R is a hydrocarbyl group, A is a silicon or a germanium atom and Cp1 represents a first cyclopentadiene or cyclopentadiene-type structure, with a alkali metal containing cyclopentadienide or cyclopentadienide-type structure to form X—R—A-Cp2Cp1, wherein Cp2 represents a second cyclopentadiene or cyclopentadiene-type structure which may be the same or different from Cp1;
(b) reacting X—R—A-Cp2Cp1 from step a) with a metal amide having the formula $M(NR_2)_4$, wherein M is Group 4 metal and R is a alkyl group having form 1 to 6 carbon atoms to form a first metallocene product;
(c) reacting the first metallocene product form step b) with a third alkali metal cyclopentadienide or a cyclopentadienide-type structure to form H-Cp3-R—A (Cp1)(CP2)M(NR_2)_2 wherein Cp3 represents a third cyclopentadiene or cyclopentadiene-type structure which may be the same or different from Cp1 or Cp2;

(d) deprotonating H-Cp3-R—A(Cp1)(Cp2)M(NR$_2$)$_2$ from step c) to form Li-Cp3-R—A(Cp1)(Cp2)M-(NR$_2$)$_2$; and (e) reacting Li-Cp3-R—A(Cp1)(Cp2)M(NR$_2$)$_2$ from step d) with Cp4MCl$_3$ to form Cp4MCl$_2$Cp3-R—A(Cp1)(CP2)M(NR$_2$)$_2$ wherein Cp4 represents a fourth cyclopentadiene or cyclopentadiene-type structure which may be the same or different from Cp1 or Cp2 or Cp3.

16. The method of claim 15 wherein in step e) two equivalents of Li-Cp3-R—A(Cp1)(Cp2)M(NR$_2$)$_2$ are reacted with a metal halide having the formula MX$_4$, wherein M is a Group 4 metal and X is a halogen, to form MCl$_2$(Cp3-R—A(Cp1)(Cp2)M(NR$_2$)$_2$)$_2$.

17. A method for preparing the catalyst complex of claim 15 comprising:

(a) reacting a lithium cyclopentadienide with a compound of the formula Cl—R—Br where each R is an alkyl group to form Cl—R-Cp1, wherein Cp1 represents a first cyclopentadiene or cyclopentadiene-type structure;

(b) reacting Cl—R-Cp1 from step a) with a Group 4 metal amide, having the formula M(NR$_2$)$_4$, wherein M is a Group 4 metal and R is a alkyl group having form 1 to 6 carbon atoms, to yield (X—R-Cp1)$_2$ M(NR$_2$)$_2$;

(c) reacting (X—R-Cp1)$_2$ M(NR$_2$)$_2$ from step b) with a second lithium cyclopentadienide to yield (H-Cp2-R-Cp1)$_2$M(NR$_2$)$_2$, where Cp2 is a cyclopentadiene or cyclopentadiene-type structure which may be the same or different from Cp1;

(d) deprotonating the product of step c) to form (Li-Cp2-R-Cp1)2M(NR$_2$)$_2$;

(e) reacting (Li-Cp2-R-Cp1)2M(NR$_2$)$_2$ from step d) with Cp3MCl$_3$ to yield (Cp3MCl$_2$Cp2-R-Cp1)$_2$M(NMe$_2$)$_2$, where Cp3 is a third cyclopentadiene or cyclopentadiene-type structure which may be the same or different from Cp1 or Cp2.

18. The metallocene complex of any of claims 1, 6 or 11, further comprising an inorganic oxide support.

19. The metallocene complex of any of claims 1, 6 or 11, further comprising an alumoxane activator or a stoichiometric activator.

20. The metallocene complex of claim 19, wherein the activator is supported on an inorganic oxide.

21. The metallocene complex of any of claims 1, 6 or 11, further comprising a methalumoxane activator supported on a silica support material.

22. The metallocene complex of any of claims 4, 9 or 13, wherein the metal bound to $L^A$ and $L^E$, and to $L^B$ and $L^F$ is zirconium; and the metal bound to $L^C$ and $L^D$ is hafnium.

23. The metallocene complex of claims 4, 9 or 13, wherein the metal bound to $L^A$ and $L^E$, and to $L^B$ and $L^F$ is hafnium; and the metal bound to $L^C$ and $L^D$ is zirconium.

24. The method of claim 15, further comprising contacting the catalyst complex with an inorganic oxide support.

25. The method of claim 22, further comprising combining an alumoxane activator or a stoichiometric activator.

26. The method of claim 15, further comprising combining a supported activator.

27. A metallocene complex comprising a first unbridged metallocene component containing a first Group 4 metal atom bonded to a ligand $L^A$ and a ligand $L^B$ and a second unbridged metallocene component containing a second Group 4 metal atom bonded to a ligand $L^C$ and a ligand $L^D$, wherein $L^A$, $L^B$, $L^C$ and $L^D$ are unsubstituted or substituted cyclopentadienyl ligands or cyclopentadienyl group containing ligands; wherein the ligand $L^B$ is linked to the ligand $L^C$ by a first linking group; and wherein the first and second metal atom are different.

28. The complex of claim 27, wherein the $L^A$ and $L^B$ ligands are bound to a zirconium atom, and the $L^C$ and $L^D$ ligands are bound to a hafnium atom.

29. The complex of claim 27, further comprising a third unbridged metallocene structure having a ligand $L^E$ and a ligand $L^F$ wherein $L^E$ and $L^F$ are unsubstituted or substituted cyclopentadienyl ligand or cyclopentadienyl group containing ligand, and wherein $L^E$ is linked to $L^D$ by a second linking group.

30. The complex of claim 29, wherein the metallocene is a zirconocene or hafnocene.

31. The complex of claim 27, further comprising an inorganic oxide support.

32. The complex of claim 27, further comprising an alumoxane activator or a stoichiometric activator.

* * * * *